United States Patent [19]
Goble et al.

[11] Patent Number: 5,129,902
[45] Date of Patent: Jul. 14, 1992

[54] ENDOSTEAL LIGAMENT RETAINER AND PROCESS

[76] Inventors: E. Marlowe Goble, 850 E. 1200 North; Karl Somers, 651 N. 150 West, both of Logan, Utah 84321

[21] Appl. No.: 511,761

[22] Filed: Apr. 20, 1990

[51] Int. Cl.⁵ ............................................... A61F 2/08
[52] U.S. Cl. ............................ 606/65; 606/60; 606/72
[58] Field of Search ............... 606/60, 65, 66, 72, 606/73, 74, 75, 76, 77, 86, 88; 623/13

[56] References Cited

U.S. PATENT DOCUMENTS

| | | | |
|---|---|---|---|
| 2,570,465 | 10/1951 | Lundholm | 606/65 |
| 4,467,478 | 8/1984 | Jurgutis | 623/13 |
| 4,640,271 | 2/1987 | Lower | 606/73 X |
| 4,744,793 | 5/1988 | Parr et al. | 623/13 |
| 4,772,286 | 9/1988 | Goble et al. | 606/66 X |
| 4,834,752 | 5/1989 | Van Kampen | 623/13 |
| 4,950,270 | 8/1990 | Bowman et al. | 606/72 |
| 4,988,351 | 1/1991 | Paulos et al. | 606/75 X |

FOREIGN PATENT DOCUMENTS

| | | | |
|---|---|---|---|
| 3538238 | 9/1986 | Fed. Rep. of Germany | 606/65 |
| 2078528 | 1/1982 | United Kingdom | 623/13 |
| 2084468A | 5/1982 | United Kingdom | |

Primary Examiner—Robert A. Hafer
Assistant Examiner—Sam Rimell
Attorney, Agent, or Firm—M. Reid Russell

[57] ABSTRACT

An endosteal ligament retainer for use in an arthroscopic surgical procedure to replace an anterior or posterior cruciate ligament, the retainer for endosteally mounting a ligament end, with or without a stent, tendon, or the like into the endosteum end of a femoral or tibial tunnel section. The embodiments of the retainer, include a disk shaped base, that can be axially pivotally mounted to a screw head end and may be holed or include upstanding arcuate walls projecting from the disk edge that are for securing a ligament end thereto, as by sewing with a suture. Alternatively, a center holed disk and screw fitted axially therethrough make up the retainer, which disk includes spaced apart radial holes for receiving a suture or sutures sewn therethrough and to a ligament end, mounting the disk across that ligament end. Additionally, the retainer can be a disk fixed across a rear end of a nail or peg to attached a ligament graft end thereto, the nail or peg leading or forward end to include spaced individual flexing rings that will collapse opposite to the direction or travel into a close fitting tunnel end to then flex outwardly, locking in the endosteum when a tensile force is applied thereto.

A driver is provided for fitting longitudinally through or alongside a ligament graft, which driver connects to either turn the screw or urge the nail or peg into the tunnel endosteum end.

17 Claims, 3 Drawing Sheets

ENDOSTEAL LIGAMENT RETAINER AND PROCESS

BACKGROUND OF THE INVENTION

1. Field of the Invention

This invention relates to ligament anchor systems and particularly to endosteal devices for use in arthroscopic surgical procedures to the knee that involve repair or replacement of an anterior or posterior cruciate ligament.

2. Prior Art

In the discipline of arthroscopic surgical procedures for repair and replacement of an anterior or posterior cruciate ligament it is often the practice to form tunnels through the distal femur and proximal tibia ends, across the ligament connection sites or points of origin, both tunnels extending through the bone cortexes. The patient's skin is opened to expose both tunnel ends and the adjacent bone cortex surfaces and a ligament is drawn through the tunnel. The ligament ends are then secured, as with a staple, or the like onto the adjacent cortex surfaces. A U.S. patent application Ser. No. 235,194, of the present inventors, entitled "Channel Ligament Clamp and System" shows such a device for securing a ligament end onto a bone mass. Additionally, other arrangements for attaching ligament ends are shown in a United Kingdom Patent No. G.B. 2,084,468A; and in an earlier patent of the present inventors U.S. Pat. No. 4,772,286.

Distinct from those earlier arrangements that involve securing a ligament beyond both tibial and femoral tunnel ends, an earlier patent of the present inventors, U.S. Pat. No. 4,870,957, and a U.S. patent application Ser. No. 07/465,914, of the present inventors, entitled "Endosteal Fixation Stud and System", provides for securing a ligament end to one tunnel cortex end that does not require opening the skin to that tunnel end. The present invention, similar to these systems, provides for endosteal fixation of a ligament end within a bone mass without the necessity of opening the patient's skin to that tunnel end. Unique therefrom the present invention employs a screw for turning in a threaded tunnel end or a nail or peg for securing it in an unthreaded tunnel end. Neither of which need to break the cortex surface at one tunnel end. The screw is for axial turning in a mount whereto a ligament or tendon is secured. The screw threaded end is turned into a tapped tunnel end that is formed in a bone endosteum. The nail or peg includes the ligament mount secured thereto and is for driving into an untapped tunnel end.

Neither screws having lag screw type threads nor nails or pegs with flexing ribs are new to orthopedic usage. A patent to Lundholm, U.S. Pat. No. 2,570,465, shows such a screw for holding bone pieces together and such nails or pegs are common for implants, such as knee prosthesis, and one such peg that is available as part of a knee prosthesis from TRICON TM is known as a FLEX-LOK TM peg. A combination of a screw for fitting axially to a ligament mount, or a nail or post mounting a ligament end axially thereto is, however, believed to be new as an endosteal ligament anchor.

SUMMARY OF THE INVENTION

It is a principal object of the present invention to provide an endosteal ligament retainer or mounting system for securing a ligament end in a bone tunnel.

Another object of the present invention is to provide a system of a ligament end retainer or mount and screw arranged axially therewith, the screw to be turned into a bone tunnel end without also turning the ligament and end retainer or mount.

Another object is to provide an endosteal ligament retainer or mount for utilization in an arthroscopic, straight tunnel surgical technique, that is suitable for mounting and maintaining a graft, either an allograft and/or prosthetic with or without a stent, in a tunnel end, which procedure does not require opening the patient's skin at that tunnel end.

Still another object of the present invention is to provide a combination of screw and ligament end retainer or mount that are axially connected to turn independently of one another.

Still another object of the present invention is to provide a nail or peg with ligament mount secured thereto to be driven into a close fitting end of a bone tunnel, securing a ligament end therein.

Still another object of the present invention is to provide a system of screw and ligament end retainer or mount, or nail or peg with mount end, that can be individually manufactured of an appropriate metal or absorbable plastic, such as DELRIN, that is suitable for human implantation.

The present invention, in one embodiment, is in an endosteal ligament end mount and screw. The device is for permanently fixing a ligament in a tunnel end of a tandem tunnel that is formed in an arthroscopic surgical procedure. Which procedure is preferable for replacing a patient's anterior or posterior cruciate ligament. Either or both the screw and ligament end retainer or mount can be formed of a metal that is suitable for human implantation or from an absorbable plastic, such as DELRIN, that is suitable for human implantation.

The ligament end retainer or mount is, in one configuration of this embodiment, a basket having a disk base and spaced apart upstanding arcuate walls that extend at right angles outwardly from opposite sections of the disk edge. The arcuate walls receive a suture, tendon, or ligament fitted therein. The disk is center holed and may be countersunk for receiving a threaded screw that is fitted axially therethrough. The undersurface of the head of which screw is to fit closely in and slide over the countersunk portion of which hole. The screw head upper face includes a walled cavity that is to receive a like faced tool end fitted therein. Which tool is for fitting longitudinally through, or to have a graft rolled therearound. The screw threaded end is to turn in a tapped tunnel end of a bone endosteum, which screw threads are preferably lag type screw threads consisting of deep and widely spaced apart threads.

Another or second embodiment of a ligament end retainer or mount of the present invention also utilizes the described screw and tool. The retainer mount of this second embodiment is like the first embodiment in that is also for turned into a tapped tunnel end, but distinct therefrom consists of a disk that is center holed to receive the screw fitted axially therethrough. Which center hole may also be countersunk or sloped to accommodate the screw head slanted under surface sliding thereover. Further, the disk includes spaced apart radial holes that are for receiving a suture, sutures, or the like, that are sewn also through a ligament or graft end for securing the disk across that ligament or graft end. The installation of which screw and disk in a tapped bone endosteum is like that described above.

A third embodiment involves a nail or peg having spaced flexing rings formed at intervals around its leading end. The nail or peg mounts a ligament on its rear most end and is to be driven into an endosteum end of the ligament tunnel. The flexing rings to flex away from the direction of travel into the endosteum, and to then flex outward, seating the ligament end. A tool like that described for the first embodiment is preferred for seating the third embodiment also, except that it is used for driving the retainer into the endosteum rather than turning.

A surgeon having formed tunnels or tunnel sections in the femur and tibia, respectively, that are suitable for receipt of a replacement an anterior or posterior cruciate ligament will align the tunnels into a straight tunnel by pivoting the lower leg relative to the upper leg. With an end of a ligament or graft, that is either an allograft and/or a prosthetic stent, secured to the retainer or end mount, and with the described tool longitudinally fitted through that ligament, the surgeon either turns the screw threaded end into the tapped tunnel end or forces the nail or post into the close fitting endosteum tunnel end. The turning of the screw of the first and second embodiments does not turn the ligament or graft or mount that remain stationary and, of course, the ligament or graft that is joined to the mount end of the nail or post does not turn during its installation where it is driven into the tunnel end. In practice, a ligament can be wound around the tool, in a fruit-roll fashion. Or the tool can be fitted alongside the ligament or graft or, between a graft, a tendon, stent, or the like, within the scope of the disclosure.

DESCRIPTION OF THE DRAWINGS

In the drawings that illustrate that which is presently regarded as the best modes for carrying out the invention.

DETAILED DESCRIPTION OF THE INVENTION

Figure 8:
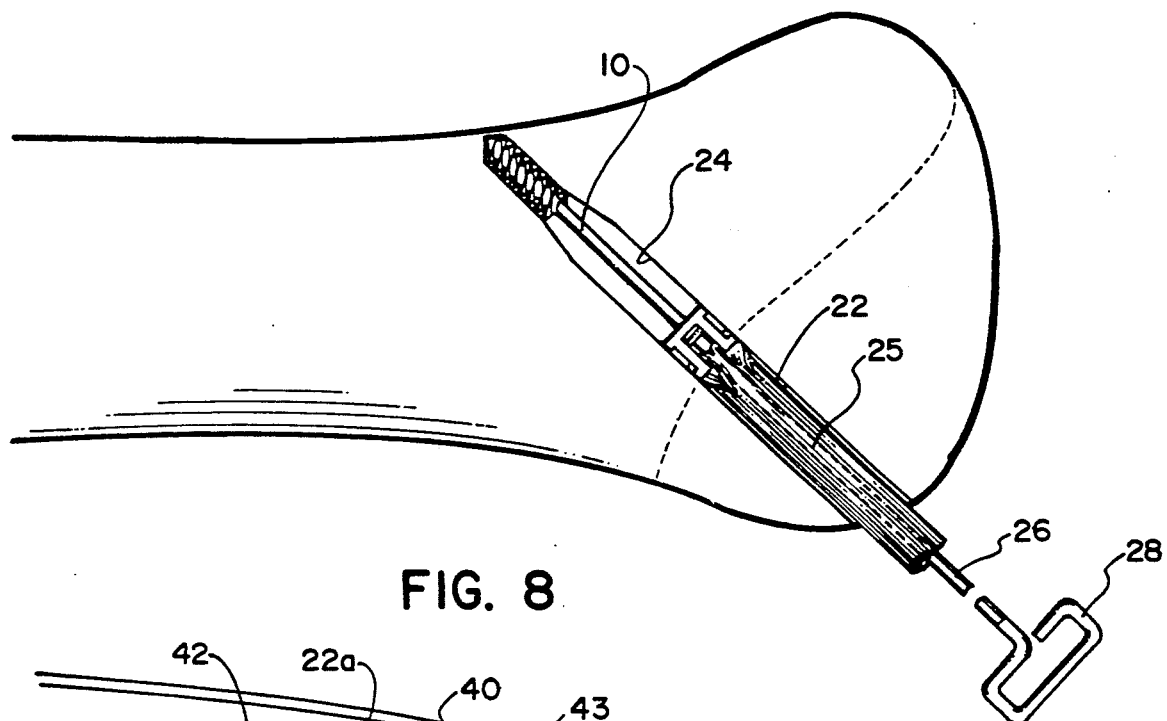
FIG. 8 shows a distal femur that has had a tunnel or tunnel section formed therein as in an anterior cruciate ligament replacement procedure and shows a ligament rolled on the turning tool or driver that is fitted into to turn a screw of the first embodiment of the endosteal ligament retainer of FIG. 5, into a tapped tunnel portion of the bone endosteum, the basket thereof shown secured to the ligament end.
Figure 10:
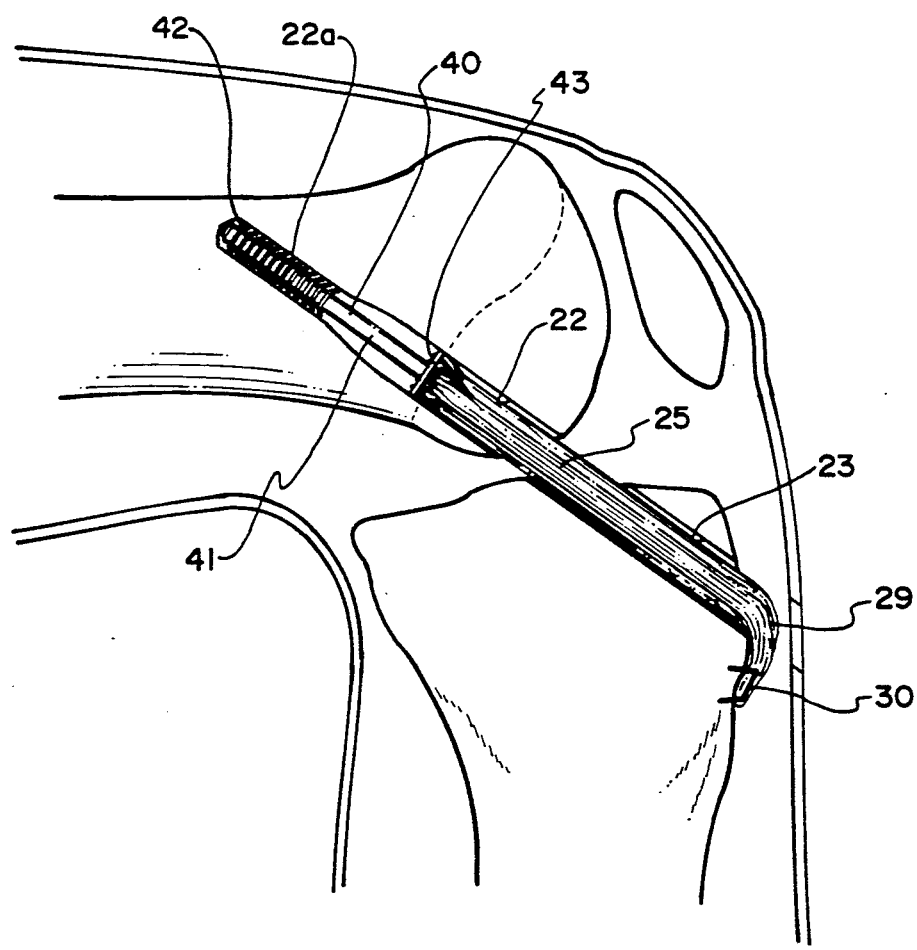
FIG. 10 shows the distal femur and proximal tibia wherethrough tunnels or tunnel sections have been formed in an anterior cruciate ligament replacement procedure, the tunnel sections shown aligned into a straight tunnel and that receives the third embodiment of the endosteal ligament retainer, mounting a ligament end thereto, urged into a close fitting tunnel end of the femur endosteum, with the opposite ligament end shown stapled to the tibial cortex surface adjacent to the tibial tunnel end.

In an arthroscopic surgical procedure for repair or replacement of an anterior or posterior cruciate ligament, as shown in FIGS. 8 and 10, tunnels 22 and 23, respectively, are formed in the distal femur, crossing the joint at the ligament points of origin and through the proximal tibia. The tunnel sections, with the leg bent appropriately, form a straight tunnel as shown best in FIG. 10.

A first embodiment of a endosteal ligament retainer or mount 10 of the present invention, hereinafter referred to as retainer, is shown in FIG. 8, being installed in a tapped endosteum end of the femoral tunnel 22. Retainer 10 is also shown in an exploded profile perspective view in FIG. 1, in FIG. 4 with a tendon 29 installed thereto, and with a graft or ligament 25, hereinafter referred to as ligament, mounted at its end in FIG. 5.

Figure 1:
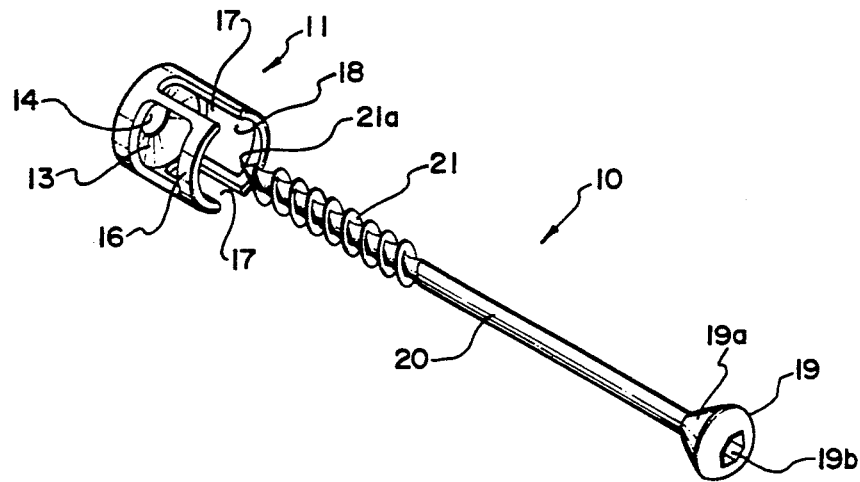
FIG. 1 is an exploded profile perspective view of a first embodiment of the present invention in an endosteal ligament retainer that is shown as a basket having a disk bottom that is center holed to accommodate a screw fitted axially therethrough.
Figure 2:
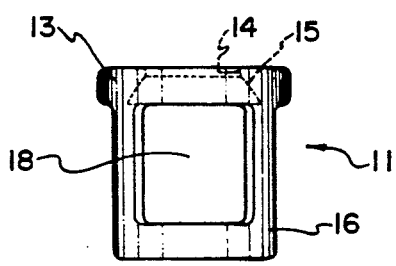
FIG. 2 is a front elevation view of the basket of FIG. 1.
Figure 3:
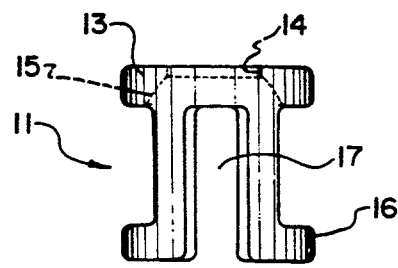
FIG. 3 is a side elevation view of the basket of FIG. 1.
Figure 9:
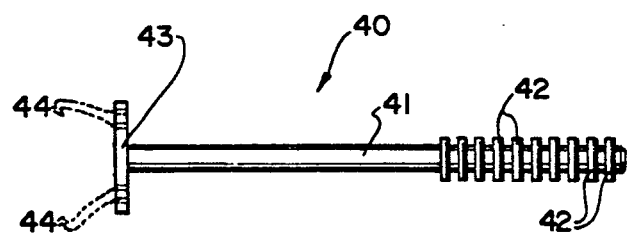
FIG. 9 shows a third embodiment of an endosteal ligament retainer of the present invention consisting of a nail or peg having spaced flexible disk segments formed at intervals around the leading end thereof with a disk that has holes formed at radial intervals secured axially across its rear end.

FIG. 1, shows the retainer 10 as consisting of a basket 11 and screw 12. Basket 11 includes a disk shaped base 13 that is center holed at 14, which center hole, as shown best in FIGS. 2 and 3, is preferably countersunk at 15. Outwardly extending arcuate walls 16 are provided to extend from opposite sides of the disk edge that are centrally open at 18 and are separated by longitudinal slots 17. So arranged, as shown best in FIG. 1, the openings 18 through the basket side walls 16 will accommodate a suture, or the like, sewn therethrough and through a ligament 25 end, as shown in FIGS. 5, 8 and 9. Or, as shown in FIG. 4, the openings 18 can receive a graft tendon 29, stent, or the like, threaded therethrough.

The described basket 11 and screw 12 are independent. As shown best in FIG. 1, the screw is for axial fitting through the hole 14 in the base 13 to where a sloping undersurface 19a of screw head 19 engages to slide freely over the countersunk portion 15 of hole 14. The screw head 19 includes a sided hole 19b formed in its top face, shown as a hexagonal sided hole, that is for receiving a like sided end 27 of a turning tool or driver 26, as shown best in FIGS. 4, 5, 7 and 8. The screw 12 includes a shaft 20 with threads 21 formed therealong to its leading or forward end opposite to head 19. The threads 21 are for turning in a tapped end of a tibia/endosteum tunnel. The threads are preferably lag type screw threads that are spaced apart from on another with the thread crust spaced well above the thread root. The threads 21 terminate in a pointed forward end 21a.

Figure 4:
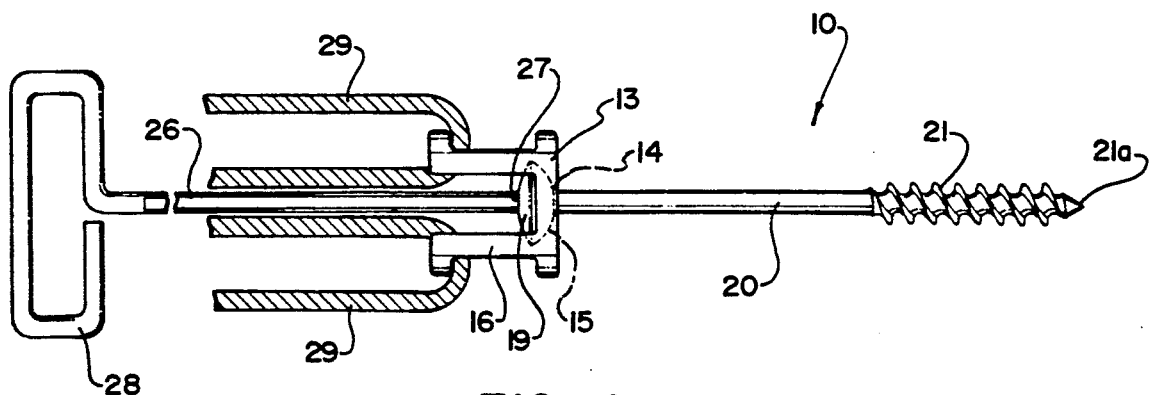
FIG. 4 is a side elevation view of the basket and screw of FIG. 1, arranged axially with a stent or stents shown looped through opposite basket side wall openings and showing an end of a turning tool fitted into the screw head.
Figure 5:
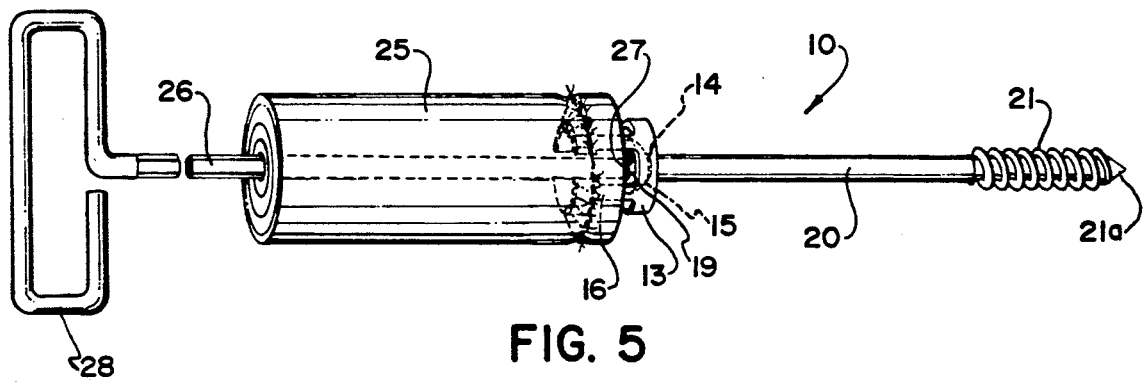
FIG. 5 is a view like FIG. 4, only showing a rolled ligament mounted at its end to the basket by a suture that is shown in broken lines sewn through the ligament end and the basket side wall openings.

FIGS. 4 and 5, show the basket 11 axially mounted to screw 12. The screw head 19 is shown fitted onto the end 27 of driver 26 that includes a handle end 28 and is for manual turning by a surgeon operator, as set out herein below. FIG. 4, shows two strands of a graft tendon 29, such as a semitendinosus or gracilis, fitted through the basket side wall openings 18, with the shaft of driver 26 fitted therebetween. The driver 26 and end 27 is shown fitted to screw head 19. FIG. 5, shows a view that is like FIG. 4, except that it shows a ligament 25, with or without a stent, that is rolled in a fruit-roll fashion around the driver 26 and with the driver end 27 fitted into the hole 19b in the head 19 of screw 12. This arrangement of retainer 10 and driver 26 with ligament 25 is shown in FIG. 8, being installed in a tapped ligament tunnel 22 end 24. Shown therein the screw threads are turned into the bone. During which turning of the screw 12, the screw only is turned, the basket 11 and the ligament 25 remaining stationary. So arranged, as shown in FIG. 8, the femoral end of anterior cruciate ligament 25, with or without a stent, is endosteally secured to the femur tunnel end, with the ligament 25 extending through the aligned femoral and tibial tunnels 22 and 23, respectively. The ligament 25 is maintained in tension and the opposite ligament end is bent, as illustrated at 29 in FIG. 10, to engage the tibial cortex surface, and is secured thereto as by driving a staple 30 into the bone. The staple 30 to span the ligament 25 to wedge it onto that bone surface.

Figure 7:
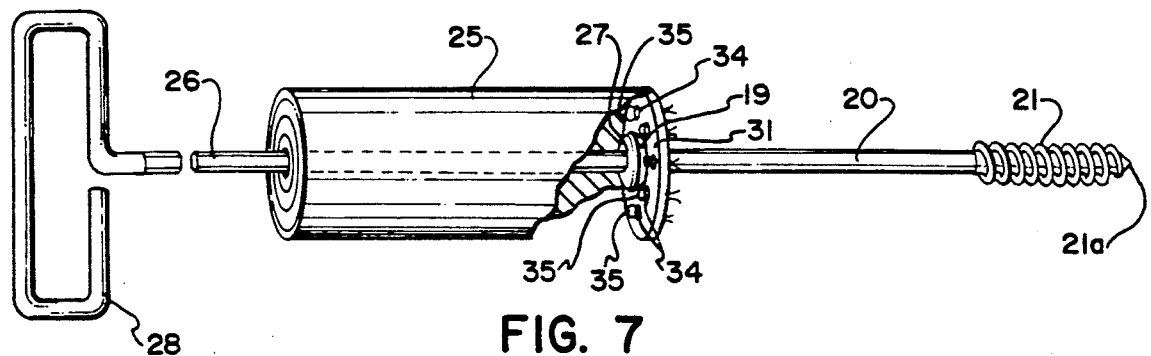
FIG. 7 is a view like FIG. 4 and 5, only showing the disk of FIG. 6 connected by sutures to the end of a ligament roll and with a turning tool or driver shown fitted longitudinally through that roll and, the driver end fitted to turn the screw that is shown positioned axially through the disk.
Figure 6:
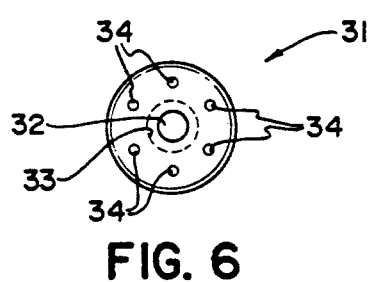
FIG. 6, shows as a second embodiment of an endosteal ligament retainer that consists of a disk for inclusion with the screw of FIG. 1.

FIG. 6, shows a second embodiment of an endosteal ligament retainer of the present invention as including a disk 31 that is for utilization with the above described screw 12. Disk 31, like basket 11, includes a center hole 32 for receiving screw 21 therethrough. The center hole 32 is preferably countersunk at 33, the screw head 19, undersurface 19a to fit against and slide thereon. The disk 31 includes radially spaced apart holes 34 that, as shown in FIG. 7, are for receiving sutures 35 sewn therethrough and through the end of ligament 25. Disk 31, like basket 11, provides for attachment to a ligament end, with or without a stent, and is for receiving screw 12 through its center hole 32. Use and installation of the disk 31 is preferably like the procedure described for basket 11 of the first embodiment with it being attached by sewing a suture or sutures 35 through the ligament end and through disk holes 34. Accordingly, the description of utilization of basket 11 and screw 12 as shown in FIG. 8, should be taken as the same for disk 31 and screw 12. Similarly, both the basket 11 and disk 31, as well as screw 12 can be manufactured from a metal of plastic material that is suitable for human implantation and the material can be a reabsorbable one such as DELRIN TM, within the scope of this disclosure.

A third embodiment of an endosteal ligament retainer is shown as a nail or peg 40 in FIG. 9 and is shown attached to a ligament 25 end in FIG. 10 that shows it installed in a ligament tunnel consisting of tunnel sections 22 and 23. The nail or peg 40 includes a straight shaft 41 whereto are arranged spaced apart flexing circular rings 42 secured at spaced intervals along the forward portion of the shaft to the leading or front end thereof. A disk 43 having radially spaced holes 44 formed therethrough is shown attached across the other on rear end of shaft 41. The disk 43 is essentially like and is utilized similarly to disk 31, in that it is attached, as by sewing, to the ligament 25 end, as shown in FIG. 10. Except that disk 43 is fixed to the shaft 41 end and accordingly does not include a center opening. Rather, the disk 43 is to receive an axially applied force to drive the nail or peg into an endosteum end 22a of tunnel 22, as shown in FIG. 10. In that process, with the nail or peg driven into the tunnel end 22a that is only somewhat larger in diameter than the shaft 41, the individual circular rings 42 on the nail or peg end are flexed away from the direction of travel, closing against the nail shaft. Such driving force can be applied through a tool, like the driver 22, except that such driver need not be appropriate for turning. The ligament 25 can be is wrapped around the driver, as illustrated in FIG. 10. Similarly, the disk 43 need not be arranged to receive such driver end therein, and depending upon the force to be applied, a handle end, like handle end 28, could be utilized to force the nail or peg 40 into the tunnel end. Or, the handle could be dispensed with and the tool end arranged to be struck, as with a hammer. The nail or peg 40 is driven to the tunnel segment 22a end. Whereafter, it is pulled back on as by an applied tensile force. Such tensile force causes the circular rings 42 to extend, flaring outwardly into the bone endosteum, securely and permanently locking the nail or peg 40 in that tunnel end 22a.

With the nail or peg 40 mounting the ligament 25 end installed, as shown in FIG. 10, the opposite ligament end that extends beyond the tibial tunnel section 23 end can be placed under an appropriate tension. The ligament is bent at 29 to where the ligament end engages the tibial cortex surface and it is attached thereto as with a staple 30, or like fastening device, as described above, completing the ligament installation procedure.

While preferred embodiments of our invention in an endosteal ligament retainer and process have been shown and described herein, it should be understood that the present disclosure is made by way of example only and that varieties and changes are possible without departing from the subject matter and reasonable equivalency thereof coming within the scope of the following claims, which claims we regard as our invention.

We claim:

1. An endosteal ligament retainer comprising, a mounting and means for securing a graft end thereto for installation into and permanently seating in an endosteum end of a ligament tunnel formed as tibial and femoral tunnel segments, said mounting consisting of a straight shaft with said means for securing a graft end thereto consisting of a disk that is arranged across a head end of said straight shaft with attachment means for attaching a graft end to extend from the surface of said disk, which attachment means consists of a wall extending at a right angle outwardly from around said disk edge, said wall having at least a plurality of openings therethrough for passing a suture means into said graft end with said straight shaft leading or front end to include thread means extending outwardly fitting into a bone endosteum at a ligament tunnel segment end; and driver means to engage the straight shaft head end for urging said straight shaft and disk with graft end attached thereto along the ligament tunnel.

2. An endosteal ligament retainer as recited in claim 1, wherein the thread means is a plurality of screw threads formed around the straight shaft from its forward end; the disk is holed at its center for axially receiving said thread shaft fitted therethrough to where said head end undersurface contacts and slides freely along the edge of said disk center hole; and the driver means is arranged for fitting into the straight shaft head end to turn said mounting.

3. An endosteal ligament retainer as recited in claim 2, wherein the straight shaft head end has a sloping undersurface and the disk center hole is countersunk to conform to the sloping undersurface of said straight shaft head; and the screw threads are lag type threads where the individual threads are spaced apart from one another.

4. An endosteal ligament retainer as recited in claim 2, wherein the wall that extends at a right angle from around the disk edges is cylindrical and is slotted at longitudinal intervals to leave a plurality of arcuate side walls that are open through there center portions as the arrangement for mounting a graft end.

5. An endosteal ligament retainer as recited in claim 1, wherein the driver means consists of a straight shaft having a coupling end for engaging the disk with a handle means on its end opposite to said coupling end.

6. An endosteal ligament retainer as recited in claim 1, wherein the driver means is a rod whearearound the graft is wound.

7. An endosteal ligament retainer as recited in claim 1, wherein the thread means consists of spaced apart outwardly extending rings that are each formed of a flexible material to collapse opposite to the direction of travel when driven into a tight fitting hole in a bone endosteum, which rings will extend into said endosteum when a tensile force is applied to said straight shaft through the attached graft.

8. An endosteal ligament retainer as recited in claim 1, wherein the mounting is formed of a material that is suitable for human implantation.

9. An endosteal ligament retainer as recited in claim 8, wherein the mounting means is formed of a biocompatible plastic material.

10. A process for endosteally suturing a ligament graft in a bone tunnel end performed during an arthroscopic surgical procedure for repairing or replacing an anterior or posterior cruciate ligament comprising, forming distal femur and proximal tibia tunnel sections that intersect the respective cruciate ligament points of origin at the knee joint, which tunnel sections, when the lower leg is bent relative to the upper leg forming a straight tunnel; terminating in either a femur or tibia tunnel section end in the bone endosteum, which tunnel end is to receive an endosteal ligament retainer secured therein; axially installing an endosteal ligament retainer to a ligament graft end and seating said endosteal retainer into the bone endosteum at the tunnel end; with the tunnel sections aligned, stretching the ligament graft to where the unattached ligament graft end is under tension and extends beyond the tunnel section opening; and securing said unattached ligament graft end to the cortex of the bone adjacent to that tunnel end.

11. A process as recited in claim 10, wherein the endosteal ligament retainer includes a disk that is for securing across a ligament graft end that axially mounts an end of a straight shaft thereto, which straight shaft, on its opposite end, includes a projection means for extending into and locking in the bone endosteum at a tunnel section end.

12. A process as recited in claim 11, wherein the disk is center holed to axially receive a screw fitted therethrough, the head end of said screw to contact and slide along the edge of said disk center hole; and a driver having an end for fitting to said screw head, and said driver is utilized to urge said screw and ligament graft section to a tapped tunnel section end in the endosteum whereat the screw is turned therein.

13. A process as recited in claim 12, wherein the ligament graft is rolled around the driver; and the driver and connected screw head are inserted through a cortex end of the femoral or tibial tunnel sections, to travel across the joint to where the screw threads are turned into the bone endosteum at the other tunnel end.

14. A process as recited in claim 11, wherein the disk is a thin center holed disk having a plurality of upstanding arcuate walls that extend at a right angles at intervals around the disk edge, which arcuate walls are each holed to receive by sewing a suture, or the like, through the openings in said arcuate walls and through the ligament graft end.

15. A process as recited in claim 14, wherein the disk is a thin flat center holed disk that includes a plurality of radially spaced apart holes that are formed therethrough for receiving a suture or sutures sewn or otherwise secured therethrough and through the ligament graft end.

16. A process as recited in claim 11, wherein the disk and straight shaft are secured together, and the projection means for extending into and locking in the bone endosteum is a plurality of individual spaced apart rings that are individually formed around the straight shaft forward or leading end and will individually flex inwardly, away from the direction of travel of the straight shaft as it is urged along the straight tunnel to the tunnel end, and will flare outwardly into said bone endosteum when a tensile force is applied to said straight shaft through that attached ligament graft.

17. A process as recited in claim 10, wherein the endosteal ligament retainer is formed of a material that is suitable to permanently remain in the body.

* * * * *